United States Patent
Gubisch et al.

(10) Patent No.: US 6,916,950 B2
(45) Date of Patent: Jul. 12, 2005

(54) PROCESS FOR PREPARING CARBOXYLIC ESTERS

(75) Inventors: Dietmar Gubisch, Marl (DE); Uwe Ernst, Marl (DE); Wilfried Bueschken, Haltern (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 09/945,736

(22) Filed: Sep. 5, 2001

(65) Prior Publication Data

US 2002/0028963 A1 Mar. 7, 2002

(30) Foreign Application Priority Data

Sep. 5, 2000 (DE) .......................................... 100 43 545

(51) Int. Cl.[7] .......................... C07C 67/36; C07C 67/00; C07C 67/08; C07C 67/12; C07C 69/52
(52) U.S. Cl. ....................................... 560/204; 560/205
(58) Field of Search .................................. 560/204, 205

(56) References Cited

U.S. PATENT DOCUMENTS

| | | | |
|---|---|---|---|
| 2,130,014 A | | 9/1938 | West et al. |
| 2,462,601 A | | 2/1949 | Bohrer |
| 3,681,434 A | | 8/1972 | Neely |
| 3,818,071 A | * | 6/1974 | Chilton et al. |
| 3,896,159 A | * | 7/1975 | Karatzer et al. |
| 3,933,630 A | * | 1/1976 | Helgorsky et al. |
| 4,241,216 A | * | 12/1980 | Bergman et al. |
| 5,648,517 A | | 7/1997 | Groeschl et al. |

FOREIGN PATENT DOCUMENTS

| | | |
|---|---|---|
| DE | 19721347 | 11/1998 |
| EP | 0 037 172 | 10/1981 |
| GB | 935279 | 8/1963 |
| GB | 1372854 | 11/1974 |
| JP | 11-189569 | 7/1999 |
| JP | 11-246486 | 9/1999 |

OTHER PUBLICATIONS

U.S. Appl. No. 09/945,736, filed Sep. 5, 2001, Gubisch et al.
U.S. Appl. No. 10/474,044, filed Oct. 15, 2003, Bueschken et al.
Vogel's Textbook of Practical Organic Chemistry. Fifth Edition. Longman Scientific and Technical. 1989.
Derwent Abstract Accession No. 70839 E/34. Dec. 22, 1980. & JP 57–106641 (Sekisui Chemi Ind KK).
Derwent Abstract Accession No. 94–116206/14. Apr. 14, 1992. & RU 2004533 C1 (Plastics Res Inst).
English Translation of Taiwanese Decision on Examination dated Sep. 9, 2003 for Application No. 90121841 (2 pp.).

* cited by examiner

*Primary Examiner*—Elvis O. Price
(74) *Attorney, Agent, or Firm*—Oblon, Spivak, McClelland, Maier & Neustadt, P.C.

(57) ABSTRACT

Carboxylic esters are prepared by a process, which comprises reacting dicarboxylic or polycarboxylic acids or their anhydrides with alcohols in a liquid medium with the concomitant removal of water formed by the esterification reaction by azeotropic distillation together with the alcohol in the medium, wherein the amount of liquid removed from the reaction medium by azeotropic distillation is replaced in whole or in part with the alcohol.

13 Claims, No Drawings

PROCESS FOR PREPARING CARBOXYLIC ESTERS

BACKGROUND OF THE INVENTION

1. Field of the Invention

The present invention relates to a batchwise process for preparing carboxylic esters by reacting dibasic or polybasic carboxylic acids or their anhydrides with alcohols. Esters of polybasic carboxylic acids, for example phthalic acid, adipic acid, sebacic acid, maleic acid, and alcohols are widely used in surface coating resins, as constituents of paints and, in particular, as plasticizers for plastics.

2. Description of the Background

It is well-known that carboxylic esters can be prepared by reacting carboxylic acids with alcohols. This reaction can be conducted autocatalytically or catalytically, for example by Bronstedt or Lewis acids. Quite independently of the type of catalysis selected, a temperature-dependent equilibrium is always formed between the starting materials (carboxylic acid and alcohol) and the products (ester and water). In order to shift the equilibrium in favor of the ester, in many esterifications an entrainer is used to remove the water formed in the reaction from the batch. If one of the starting materials (alcohol or carboxylic acid) boils lower than the ester formed and forms a miscibility gap with water, a starting material can be used as entrainer and after water is removed, can be recirculated back to the batch. In the esterification of dibasic or polybasic acids, generally the alcohol used is the entrainer. For many applications the ester thus prepared must have a low acid number, that is to say the reaction of the carboxylic acid should proceed virtually quantitatively. Otherwise the yield is decreased and the acid must be removed, for example by neutralization. This procedure is complex and can lead to byproducts which require disposal. In order to obtain as high as possible a conversion of the carboxylic acid, esterifications are generally conducted with an excess of alcohol. However, excess alcohol has the disadvantage that in the case of low-boiling alcohols, the reaction temperature at atmospheric pressure is so low that the reaction rate is too low for an industrial process. In order to counteract this effect, the reaction can be conducted under pressure, which leads to higher apparatus costs. A further disadvantage is that, with increasing excess of alcohol, the maximum possible concentration of the target product in the reaction vessel decreases and thus the batch yield decreases. Furthermore, the excess alcohol must be separated from the ester, which is time and energy consuming.

Esterification reactions for the plasticizer esters, dioctyl phthalate (DOP) and diisononyl phthalate (DINP) with organotitanium catalysis, are well-studied reactions and are described, for example, in GB 2 045 767, DE 197 21 347 or U.S. Pat. No. 5,434,294.

These processes comprise the following steps:

reaction of one molecule of phthalic anhydride with one molecule of alcohol to give the half ester (ester carboxylic acid), autocatalytic;

addition of titanium catalyst, for example, n-butyl titanate, for the reaction of one molecule of half ester with one molecule of alcohol with elimination of water to give the diphthalate;

simultaneous removal of the water of reaction by distilling an alcohol/water azeotrope;

destruction of the catalyst by addition of base;

removal of excess alcohol by distillation;

removal of catalyst residue by filtration; and purification of the phthalic diester by distillation, for example steam distillation.

These processes are batch processes and are not yet optimized with respect to maximum utilization of the reactors, that is to say space-time yield. A need continues to exist for an improved method of conducting the batch synthesis of esters at higher space-time yields. i.e., short reaction times and high batch yields.

SUMMARY OF THE INVENTION

Accordingly, one object of the present invention is to provide a batchwise esterification process which results in improved space-time yield of ester product.

Briefly, this object and other objects of the present invention as hereinafter will become more readily apparent can be attained by a process for preparing carboxylic esters, which comprises reacting dicarboxylic or polycarboxylic acids or their anhydrides with alcohols in a liquid medium with the concomitant removal of water formed by the esterification reaction by azeotropic distillation together with the alcohol in the medium, wherein the amount of liquid removed from the reaction medium by azeotropic distillation is replaced in whole or in part with the alcohol.

DETAILED DESCRIPTION OF THE PREFERRED EMBODIMENTS

The central feature of the present invention is that in the preparation of carboxylic esters by reacting dicarboxylic acids or polycarboxylic acids or their anhydrides with alcohols, the water of reaction is removed by azeotropic distillation together with the alcohol, while replacing the amount of liquid removed from the reaction by the azeotropic distillation in whole or in part with the alcohol. The amount of liquid designated below is the volume of liquid which is removed from the reaction by azeotropic distillation and principally consists of water of reaction and alcohol.

Complete replacement of the amount of liquid removed from the esterification reactor is preferred. This can be achieved, for example, by level-controlled feed of alcohol into the reactor. For technical reasons, complete replacement of the amount of liquid removed may not be achievable or may only be achievable with difficulty. In these cases, the amount of liquid removed is only partially replaced, for example, only the alcohol, but not the reaction water removed, but, in all cases, is replaced by more than 90%, preferably from 95% to 98%.

It may also be necessary to recirculate more than the amount of liquid removed by distillation to the reactor, that is to say, in addition to the amount of alcohol removed, the reaction water is replaced, and, in addition, further alcohol is added. In this embodiment, from 110% to 100%, preferably 105% to 100%, of the amount of liquid removed is replaced by alcohol.

The present process has the advantage that, compared with known batchwise processes, the reaction rate is increased. As a result the cycle time can be reduced, which gives a higher space-time yield of ester product.

The present process is applicable in principle to all esterification reactions in which the water of reaction is separated by distillation together with an alcohol.

In the present process, the acid component used is dicarboxylic acids, polycarboxylic acids or their anhydrides. In the case of polybasic carboxylic acids, partial anhydrides can also be used. It is also possible to use mixtures of carboxylic acids and anhydrides. The acids can be aliphatic, carbocyclic, heterocyclic, saturated or unsaturated, and also aromatic acids.

Aliphatic carboxylic acids should have at least 4 carbon atoms.

Suitable examples of aliphatic carboxylic acids and their anhydrides include maleic acid, fumaric acid, maleic anhydride, succinic acid, succinic anhydride, adipic acid, suberic acid, trimethyladipic acid, azelaic acid, decanedioic acid, dodecanedioic acid, brassylic acid. Suitable examples of carbocyclic acid compounds include hexahydrophthalic anhydride, hexahydrophthalic acid, cyclohexane-1,4-dicarboxylic acid, cyclohex-4-ene-1,2-dicarboxylic acid, cyclohexene-1,2-dicarboxylic anhydride, 4-methylcyclohexane1,2-dicarboxylic acid, 4-methylcyclohexane-1,2-dicarboxylic anhydride, 4-methylcyclohex-4-ene-1,2-dicarboxylic acid and 4-methylcyclohex-4-ene-1,2-dicarboxylic anhydride. Suitable examples of aromatic acid compounds include phthalic acid, phthalic anhydride, isophthalic acid, terephthalic acid, trimellitic acid, trimesic acid, pyromellitic acid, pyromellitic anhydride and naphthalene dicarboxylic acids.

In the present process, preferably, branched or unbranched aliphatic alcohols having 4 to 13 carbon atoms are used. The alcohols are monohydric and can be secondary or primary. The alcohols may originate from various sources. Suitable starting materials include, for example, fatty alcohols, alcohols from the Aldol process or alcohols or alcohol mixtures which were produced by hydrogenation of saturated or unsaturated aldehydes, in particular those alcohols whose synthesis includes a hydroformylation step.

Alcohols which may used in the inventive process include, for example, n-butanol, isobutanol, n-octanol (1), n-octanol (2), 2-ethylhexanol, nonanols, decyl alcohols or tridecanols produced by hydroformylation or aldol condensation and subsequent hydrogenation. The alcohols may be used as a pure compound, as a mixture of isomeric compounds or as a mixture of compounds having a different number of carbon atoms.

Preferred starting alcohols are mixtures of isomeric octanols, nonanols or tridecanols, the latter being able to be produced from the corresponding butene oligomers, in particular oligomers of unbranched butenes, by hydroformylation and subsequent hydrogenation. The butene oligomers can be prepared, in principle, by three processes. Acid-catalyzed oligomerization, in which, industrially, for example, a zeolite or phosphoric acid is used on a support, gives the most highly branched oligomers. When unbranched butenes are used, for example, a $C_8$ fraction is formed which essentially consists of dimethylhexenes (WO 92/13818). A process which is also carried out worldwide is oligomerization using soluble Ni complexes, known as the DIMERSOL process (B. Comils, W. A. Herrmann, Applied Homogeneous Catalysis with Organometallic Compounds, pages 261–263, Verlag Chemie 1996). In addition, oligomerization is practiced on nickel fixed-bed catalysts, for example, the OCTOL process (Hydrocarbon Process., Int. Ed. (1986) 65 (2. Sect. 1), pages 31–33).

Very particularly preferred starting materials for the present esterification are mixtures of isomeric nonanols or mixtures of isomeric tridecanols which are prepared by oligomerizing unbranched butenes to give $C_8$ olefins and $C_{12}$ olefins by the Octol process, with subsequent hydroformylation and hydrogenation.

The inventive esterification can be conducted under autocatalytic or catalytic conditions. Esterification catalysts which can be used are Lewis acids or Bronstedt acids or organometallic substances which do not necessarily need to act as acids. Preferred esterification catalysts are alkoxides, carbonate salts or chelate compounds of titanium or zirconium, the catalyst molecule being able to contain one or more metal atoms. In particular, tetraisopropyl orthotitanate and tetrabutyl orthotitanate are used.

Esterification is conducted in a reaction vessel in which the reaction batch is intensively mixed using an agitator or recirculation pump. The starting materials and the catalyst can be charged into the reactor simultaneously or sequentially. If one starting material is solid at the charging temperature, it is expedient to introduce the liquid starting component first. Solid starting materials can be fed as powder, granules, crystals or melt. In order to shorten the batch time, it is advisable to start the heating during charging. The catalyst can be introduced in pure form or as solution, preferably dissolved in one of the starting materials, at the start or only after the reaction temperature has been reached. Carboxylic anhydrides frequently react with alcohols, even autocatalytically, that is to say non-catalyzed, to give the corresponding ester carboxylic acids (half esters), for example phthalic anhydride reacts to give phthalic acid monoester. Therefore, a catalyst is frequently not required until after the first reaction step.

The alcohol to be reacted, which serves as entrainer, can be used in a stoichiometric excess, preferably from 5% to 50%, particularly preferably from 10% to 30%, of the stoichiometrically required amount.

The catalyst concentration depends on the type of catalyst. In the case of the titanium compounds preferably used, the catalyst concentration ranges from 0.005% to 1.0% by weight, based on the reaction mixture, in particular from 0.01% to 0.3% by weight.

The reaction temperatures when titanium catalysts are used range from 160° C. to 270° C. The choicest temperatures depend on the starting materials, reaction progress and the catalyst concentration. They can readily be determined for each individual case by experiment. Higher temperatures increase the reaction rates and favor side reactions, for example, elimination of water from alcohols, or formation of colored byproducts. It is necessary, in order to remove the reaction water, that the alcohol be removed by distillation from the reaction mixture. The desired temperature or the desired temperature range can be set by the pressure in the reaction vessel. In the case of low-boiling alcohols, the reaction is, therefore, conducted at superatmospheric pressure, and in the case of higher-boiling alcohols, at reduced pressure. For example, in the reaction of phthalic anhydride with a mixture of isomeric nonanols, a temperature range of 170° C. to 250° C. in the pressure range of from 1 bar to 10 mbar is employed.

The amount of liquid to be recycled to the reaction medium of the invention can consist in part or in whole of alcohol which is produced by work-up of the azeotropic distillate. It is also possible to carry out the work-up at a later time and to replace the amount of liquid removed in whole or in part by fresh alcohol, that is to say alcohol being provided from a storage vessel.

In other embodiments of the invention, the liquid which is separated is worked-up to produce the alcohol.

During the reaction, an alcohol-water mixture is removed by distillation from the reaction mixture as an azeotrope. The vapors leave the reaction vessel via a short column (internals or packing, 1 to 5, preferably 1 to 3, theoretical plates) and are condensed. The condensate can be separated into an aqueous phase and an alcoholic phase, which can make cooling necessary. The aqueous phase is removed by separation and can, if appropriate after work-up, be discarded or used as stripping water in the after-treatment of the ester.

The alcoholic phase which is produced after separating the azeotropic distillate can be recirculated to the reaction vessel in part or in whole. In practice, control of the reaction by a level controller has proved itself for feeding the alcohol to the reactor.

It is possible to replace the amount of liquid removed by the azeotropic distillation completely or in part by separating the liquid which has been separated into an alcohol phase and a water phase and recirculating the alcohol phase to the esterification reaction.

Optionally, fresh alcohol can be added to the alcohol phase and removed by separation.

There are various ways in which the alcohol can be fed to the esterification reaction. The alcohol can be added, for example, as a reflux to the column. Another possibility is to pump the alcohol, if appropriate after heating, into the liquid reaction mixture. Separation of the water of reaction decreases the reaction volume in the apparatus. In the ideal case, during the reaction, as much alcohol is replenished as corresponds to the volume of the distillate removed by separation (water and if appropriate alcohol), so that the fluid level in the reaction vessel remains constant. In the present process, by increasing the excess alcohol, the equilibrium is shifted in the favor of the full esters.

When the reaction is complete, the reaction mixture, which essentially consists of full ester (target product) and excess alcohol, comprises, in addition to the catalyst and/or its secondary products, small amounts of ester carboxylic acid(s) and/or unreacted carboxylic acid.

To work up these crude ester mixtures, the excess alcohol is removed, the acidic compounds are neutralized, the catalyst is destroyed and the resultant solid byproducts are removed by separation. The majority of the alcohol is removed by distillation at atmospheric pressure or under reduced pressure. The last traces of the alcohol can be removed, for example, by steam distillation, in particular in the temperature range from 120 to 225° C. The alcohol can be separated as the first or last work-up step.

The acidic substances, such as carboxylic acids, ester carboxylic acids or, if appropriate, the acid catalysts, are neutralized by adding basic compounds of the alkali metals and alkaline earth metals. These are used in the form of their carbonates, hydrogencarbonates or hydroxides. The neutralizing agent can be used in solid form, or preferably as solution, in particular as aqueous solution. Here, sodium hydroxide solution is frequently used in the concentration range from 1% to 30% by weight, preferably from 20% to 30% by weight. The neutralizing agent is used in an amount which corresponds to the stoichiometrically required amount to four times the stoichiometrically required amount, in particular the stoichiometrically required amount to twice the stoichiometrically required amount, as determined by titration. When the titanium catalysts are used, the neutralizing agent converts these catalysts into solid filterable substances.

Neutralization can be conducted immediately after ending the esterification reaction or after removing the majority of the excess alcohol by distillation. Preference is given to neutralization with sodium hydroxide solution immediately after completion of the esterification reaction at temperatures above 150° C. The water introduced with the alkaline solution can then be removed by distillation together with the alcohol.

The solids present in the neutralized crude ester can be separated by centrifuging, or preferably by filtration.

Optionally, after the esterification reaction, a filter aid and/or absorbent can be added during work-up for improved filterability and/or removal of colored substances or other byproducts.

The process described here can be conducted in one vessel or in a plurality of sequentially-connected vessels. Thus, for example, esterification and work-up can proceed in different vessels. When carboxylic anhydrides are used, there is the option of conducting the reactions to give the half ester and the diester in different reactors.

The esters thus produced from polybasic carboxylic acids, for example phthalic acid, adipic acid, sebacic acid, maleic acid, and alcohols are widely used in resin coatings, as constituents of paints and, in particular, as plasticizers for plastics. Suitable plasticizers for PVC are diisononyl phthalates and dioctyl phthalates. The use of the inventively prepared esters for these purposes is also an aspect of the invention.

The alcohol separated during work-up can, if appropriate after discharge of a portion, be used for the next batch.

Having now generally described this invention, a further understanding can be obtained by reference to certain specific examples which are provided herein for purposes of illustration only and are not intended to be limiting unless otherwise specified.

EXAMPLES

The esterification reactor employed in the examples consists of a stirred tank having a heating coil (40 bar steam), a separation system for the reaction water/alcohol separation and a return line for excess alcohol. The apparatus is purged with nitrogen to eliminate oxygen prior to charging the reactants.

Esterification of phthalic anhydride with a mixture of isomeric isononanols to give diisononyl phthalate (DINP)

Example 1 (Comparative Example)

Starting quantities:

1,000 kg of phthalic anhydride (liquid)

2,430 kg of isononanol 1 kg of butyl titanate

As soon as 400 kg of isononanol had been charged into the reactor, heating was started. Phthalic anhydride in liquid form and the remaining amount of alcohol (2 030 kg) were fed into the reactor simultaneously. After the reaction mixture had achieved a temperature of 120° C., the titanium catalyst was added. At 170° C. the mixture began to boil. At this time point the maximum level of 80% was also established in the reactor. During the esterification, water was released and removed by distillation as isononanol azeotrope. The acid number of the reaction mixture decreased from an initial value of 100 mg KOH/g at the start of boiling to 10 mg KOH/g after 150 minutes, 1 mg/g KOH after 290 minutes and 0.5 mg KOH/g after 330 minutes. The fluid level in the reactor at this time was still 76%.

Example 2 (Invention)

Starting quantities:

1,000 kg of phthalic anhydride (liquid)

2,430 kg of isononanol 110 kg of isononanol (supplement)

1 kg of butyl titanate

As soon as 400 kg of isononanol had been introduced into the reactor, heating was started. Phthalic anhydride in liquid form and the remaining amount of alcohol (2,030 kg) were fed into the reactor simultaneously. After the reaction mixture had achieved a temperature of 120° C., the titanium catalyst was added. At 170° C. the mixture began to boil. At this time point the maximum level of 80% was also established in the reactor. During the esterification, water was released and distilled as isononanol azeotrope. At a fluid level of 78% in the reactor (approximately 2 h after the start of boiling), the level was brought back to 80% by the addition of fresh isononanol (not present in the starting amount) and this level was maintained by further supplementation of isononanol until the end of the reaction. When the reaction was completed (AN=0.5), the isononanol excess was 110 kg higher than in Comparative Example 1. The acid number of the reaction mixture decreased in this batch from an initial value of 100 mg KOH/g at the start of boiling to 10 mg KOH/g after 150 minutes, 1 mg KOH/g after 270 minutes and 0.5 mg KOH/g after 300 minutes.

Therefore, the esterification time is decreased by the present process by 30 minutes or by 9%. (Yield based on phthalic anhydride is greater than 99.8%)

Esterification of phthalic anhydride with 2-ethylhexanol to give bis (2ethylhexyl)phthalate (DOP)

Example 3 (Comparative Example)

Starting quantities:

1,070 kg of phthalic anhydride (liquid)

2,350 kg of 2-ethylhexanol 1 kg of butyl titanate

As soon as 400 kg of 2-ethylhexanol had been introduced into the reactor, heating was started. Phthalic anhydride in liquid form and the remaining amount of alcohol (1 950 kg) were fed into the reactor simultaneously. After the reaction mixture had reached a temperature of 120° C., the titanium catalyst was added. At 170° C., the mixture began to boil. At this time the maximum fluid level of 80% was also established in the reactor. During the esterification, water was released and distilled as an azeotrope with 2-ethylhexanol. The acid number of the reaction mixture decreased from an initial value of 110 mg KOH/g at the start of boiling to 10 mg KOH/g after 165 minutes, 1 mg KOH/g after 320 minutes and 0.5 mg KOH/g after 365 minutes. The level in the reactor at this time was still 76%.

Example 4 (Invention)

Starting quantities:

1,070 kg of phthalic anhydride (liquid)

2,350 kg of 2-ethylhexanol 1 kg of butyl titanate

As soon as 400 kg of 2-ethylhexanol had been introduced into the reactor, heating was started. Phthalic anhydride in liquid form and the remaining amount of alcohol (1,950 kg) were fed into the reactor simultaneously. After the reaction mixture had achieved a temperature of 120° C., the titanium catalyst was added. At 170° C., the mixture began to boil. At this time point the maximum level of 80% was also established in the reactor. During the esterification water was released and distilled as an azeotrope with 2-ethylhexanol. At a level of 78% in the reactor (approximately 2 h after the start of boiling), the level was brought back to 80% with fresh 2-ethylhexanol (not present in the starting amount) and this level was maintained by further supplementation of 2-ethylhexanol until the end of the reaction. When the reaction was completed (AN=0.5), the 2-ethylhexanol excess was 120 kg higher than in Comparative Example 3. The acid number of the reaction mixture decreased in this batch from an initial value of 110 mg KOH/g at the start of boiling to 10 mg KOH/g after 165 minutes, 1 mg KOH/g after 300 minutes and 0.5 mg KOH/g after 325 minutes.

This pair of examples shows that the esterification time is decreased by the present process by 40 minutes or 11% (yield greater than 99.8% based on phthalic anhydride).

The disclosure of German priority Application No. 100 43 545.9 filed Sep. 5, 2000 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein

What is claimed as new and is intended to be secured by Letters Patent is:

1. A process for preparing carboxylic esters, which comprises:

in a batch process, reacting polycarboxylic acids or their anhydrides with alcohols in a liquid medium with the concomitant removal of water formed by the esterification reaction by azeotropic distillation together with the alcohol in the medium, wherein the volume amount of liquid azeotrope mixture of water and alcohol removed from the reaction medium by azeotropic distillation is entirely replaced with the alcohol, whereby the volume amount of water azeotropically removed during the batch process at least corresponds to the volume amount of water formed by the reaction of the starting quantity of polycarboxylic acids or anhydrides thereof and the alcohol down to a reduced amount of polycarboxylic acids or anhydrides thereof in the terminal stages of the ester forming reaction indicated by an acid number value of 0.5 mg KOH/g.

2. The process as claimed in claim 1, wherein a portion of the amount of liquid removed by azeotropic distillation is supplemented by separating the liquid azeotrope mixture of water and alcohol which has been removed into a water phase and an alcohol phase, and then recirculating the alcohol phase to the esterification reaction medium.

3. The process as claimed in claim 1, wherein the amount of liquid azeotrope mixture of water and alcohol removed by azeotropic distillation is supplemented entirely by separating the liquid azeotrope mixture of water and alcohol which has been removed into a water phase and an alcohol phase, and then recirculating the alcohol phase, additionally admixed with fresh alcohol, to the esterification reaction medium.

4. The process as claimed in claim 1, wherein the amount of liquid azeotrope mixture of water and alcohol removed from the reaction by azeotropic distillation is entirely replaced by fresh alcohol.

5. The process as claimed in claim 1, wherein the polycarboxylic acid or polycarboxylic acid anhydride is phthalic acid or phthalic anhydride.

6. The process as claimed in claim 1, wherein the alcohol is n-butanol, isobutanol, n-octanol (1), n-octanol (2), 2-ethylhexanol, nonanols, decyl alcohols or tridecanols.

7. The process as claimed in claim 1, wherein the polycarboxylic acid or anhydride is an aliphatic polycarboxylic acid or anhydride selected from the group consisting of maleic acid, fumaric acid, maleic anhydride, succinic acid, succinic anhydride, adipic acid, suberic acid, trimethyladipic acid, azelaic acid, decanedioic acid, dodecanedioic acid and brassylic acid.

8. The process as claimed in claim 1, wherein the polycarboxylic acid or anhydride is a carbocyclic acid or anhydride compound selected from the group consisting of hexahydrophthalic anhydride, hexahydrophthalic acid, cyclohexane-1,4-dicarboxylic acid, cyclohex-4-ene-1,2-dicarboxylic acid, cyclohex-4-ene-1,2-dicarboxylic anhydride, 4-methylcyclohexane-1,2-dicarboxylic acid, 4-methylcyclohexane-1,2-dicarboxylic anhydride, 4-methylcyclohex-4-ene-1,2-dicarboxylic acid and 4-methylcyclohex-4-ene-1,2-dicarboxylic anhydride.

9. The process as claimed in claim 1, wherein the polycarboxylic acid or anhydride is an aromatic acid or anhydride compound selected from the group consisting of phthalic acid, phthalic anhydride, isophthalic acid, terephthalic acid, trimellitic acid, trimesic acid, pyromellitic acid, pyromellitic anhydride and naphthalene dicarboxylic acids.

10. The process as claimed in claim 1, wherein the reaction is conducted at a temperature ranging from 160 C to 270 C.

11. The process as claimed in claim 1, wherein the reaction is conducted at a temperature ranging from 170 C to 270 C.

12. The process as claimed in claim 1, wherein the alcohol reactant is a $C_{4-13}$-branched or unbranched aliphatic alcohol.

13. The process as claimed in claim 1, which further comprises neutralizing excess acid or anhydride remaining at the end of the esterification reaction by the addition of base to the medium.

* * * * *